United States Patent [19]

Lund

[11] 4,219,027

[45] Aug. 26, 1980

[54] SUBCUTANEOUS ELECTRODE STRUCTURE

[76] Inventor: Robert A. Frosch, Administrator of the National Aeronautics and Space Administration, with respect to an invention of Gordon F. Lund, San Jose, Calif.

[21] Appl. No.: 3,693

[22] Filed: Jan. 16, 1979

[51] Int. Cl.³ .............................................. A61B 5/04
[52] U.S. Cl. .................................................. 128/642
[58] Field of Search ........ 128/639, 640, 642, 783–785, 128/802

[56] References Cited

U.S. PATENT DOCUMENTS

| | | | |
|---|---|---|---|
| 2,985,172 | 5/1961 | Jones | 128/784 |
| 3,170,459 | 2/1965 | Phipps et al. | 128/640 |
| 3,496,929 | 2/1970 | Domingues | 128/639 |
| 3,543,761 | 12/1970 | Bradley | 128/784 X |
| 3,565,059 | 2/1971 | Hauser et al. | 128/640 |
| 4,011,861 | 3/1977 | Enger | 128/642 |

*Primary Examiner*—Lee S. Cohen
*Attorney, Agent, or Firm*—Darrell G. Brekke; John R. Manning; Armand McMillan

[57] ABSTRACT

A subcutaneous electrode structure particularly suitable for a chronic implant and for taking a low noise electrocardiogram of an active animal such as a rat, dog, monkey, cow or the like, comprises a thin inflexible, smooth disc of stainless steel having a diameter as of 5 to 30 mm, which is sutured in place to the tissue of the animal being monitored. The disc electrode includes a radially directed slot extending in from the periphery of the disc for approximately ⅓ of the diameter. Electrical connection is made to the disc by means of a flexible lead wire that extends longitudinally of the slot and is woven through apertures in the disc and held thereto at the terminal end by means of a spot-welded tab. Within the slot, an electrically insulative sleeve, such as silicone rubber, is placed over the wire. The wire with the sleeve mounted thereon is captured in the plane of the disc and within the slot by means of crimping tabs extending laterally of the slot and over the insulative wire. The marginal lip of the slot area of the disc is apertured and an electrically insulative potting material, such as silicone rubber, is potted in place overlaying the wire slot region and through the apertures in the electrode.

11 Claims, 3 Drawing Figures

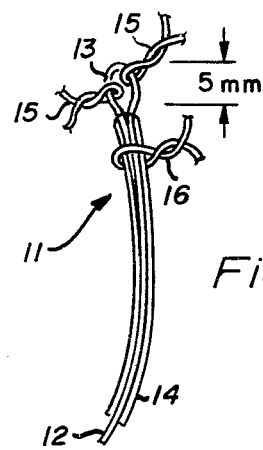
Fig_1 PRIOR ART
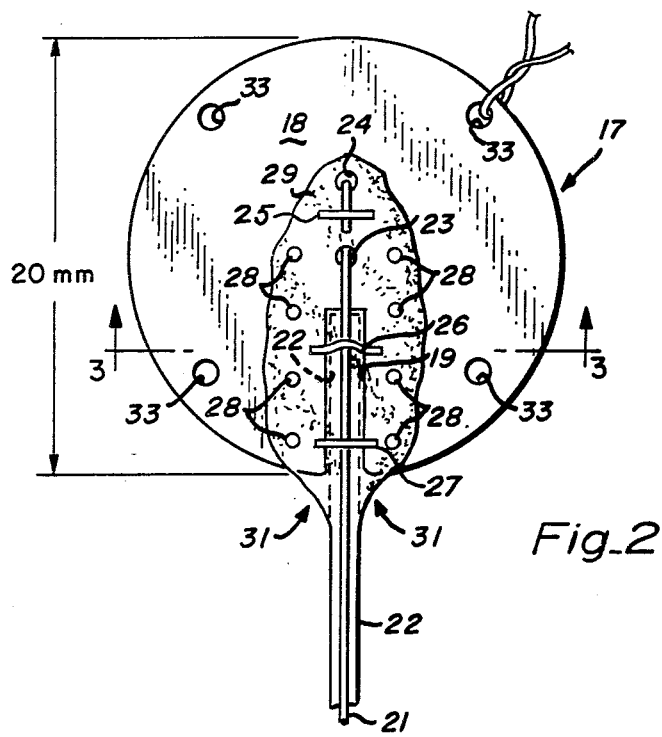
Fig_2
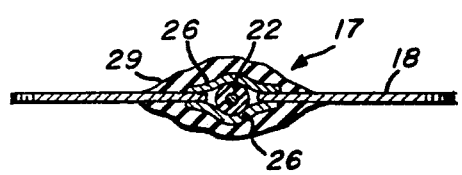
Fig_3

SUBCUTANEOUS ELECTRODE STRUCTURE

BACKGROUND OF THE INVENTION

1. Field of the Invention

The present invention relates in general to subcutaneous electrode structures and, more particularly, to an improved electrode structure useful as a chronic implant for taking electrocardiograms of active animals.

2. Description of the Prior Art

Radiotelemetry has long been applied to physiological monitoring. Biotelemetry systems are especially suited for the monitoring of unrestrained animals. Implanted biotelemetry systems have been employed to monitor temperature, pressure and biopotentials. Heretofore, there has not been a suitable internal electrode for providing electrocardiograms (ECG or EKG) in active animals wherein the electrode is chronically implanted.

Conventional ECG electrodes tend to produce movement artifacts (movement generated noise) so that it is difficult to obtain quality data when the test subject is active. Therefore, it is desired to obtain an improved chronically implanted, subcutaneous electrode structure which has reduced electrical noise associated therewith.

In the past, designers of external electrodes were concerned with maintaining a high amplifier input impedance to electrode impedance ratio to prevent loading, signal distortion and extraneous 60-cycle noise. Therefore, they chose external electrodes with large distributed surface areas in order to compensate for the high contact impedance caused by the cornified epithelium of the skin. Of course, as the electrode area was increased, the contact impedance was reduced. The problem caused by the skin barrier was greatly reduced with the advent of electrolytic jellies and pastes as well as electrode designs featuring pointed projections to pierce the cornified epithelium. The contact areas of modern external electrodes, as a result, are often much smaller in appearance than the old style clinical plate electrodes. 60-cycle stray noise is seldom a problem with internal electrodes. Further, internal electrodes do not encounter a cornified epithelium. Investigators such as Geddes and Baker have stated (*Med & Biol. Engng.,* Vol. 4, pp. 439–450, Pergamon Press, 1966) that subcutaneously implanted stainless steel needle electrodes have a low enough impedance to prevent amplifier loading and signal distortion.

Prior suggestions on how to reduce the problem of movement artifacts seem to stress that a major requirement is to protect, to isolate, to stabilize, and/or to limit the electrode-electrolyte interface from disturbances. The interface involves a half cell potential that is imparted to an electrode through reversible oxidation-reduction reactions. This gives rise to an alignment in charge distribution. The process is discussed in most chemistry textbooks and is commonly known in the context of batteries. When disturbances of this electrochemical interface occur, the half cell potential of one electrode relative to the other is altered and these transient differences in potential between the two electrodes are believed to be the cause of artifacts.

Many prior art ECG electrode designs have been predicated on half cell considerations. The majority of the available information is presented in the context of external ECG electrodes. In the past, the two most often emphasized approaches for the design of external electrodes are to use low mass to reduce problems of inertia and to use recessed electrodes in combination with an electrolytic substance that allows for lifting the interface away from and protecting it from the movements of the underlying skin. For example, it is stated in "Principles of Applied Biomedical Instrumentation," 2nd Edition, L. A. Geddes and L. E. Baker, John Wiley & Sons, New York, 1975, pp. 226–227, that when biopotential measurements are to be made on active subjects "it is important to make the electrodes as small and light as possible."

By far the most prevalent means for attempting to solve the problem of movement artifacts in internal electrodes was to provide an electrode of a very small surface area which could be anchored quite securely against the tissue. Electrodes of this type include small hooked wires, needles, or wire loops which are discussed in "Medical Instrumentation," John G. Webster, Houghton Mifflin Company, Boston, 1978, pp. 250–255.

It is also known from the prior art to employ, as a subcutaneous electrode, a porous plate composed of a tissue-compatible implantable material such as platinum. Such an implantable electric terminal for organic tissue is disclosed in U.S. Pat. No. 4,011,861, Mar. 15, 1977. The porous electrode permits body electrolytes and/or tissue containing blood capillaries to contact the electrically conductive material of the electrode through the porous material or layer. Electrical connection is made to the electrode by means of a rod bonded to the disc in the central region thereof and extending normally from a major face of the electrode. Such an electrode structure is unsuited for a chronically implanted, subcutaneous electrode for several reasons. Its physical configuration and size when placed between layers of tissue would place pressure on the tissue that would result in time to necrosis of the tissue and eventual rejection or displacement in location. The connection of the rod structure to the porous material and the connection of the rod to some necessary lead conductor are not stress relieved and flexible. Thus with movement, the interface between the tissue and electrode would be distorted and result in artifacts and tissue damage. There are no indicated methods or apparatus for suturing the electrode in place so as to insure a fixed initial location before tissue imbedding occurs. Porous materials are hard to clean and to keep clean during a surgical implant. Should infection occur, these pores would serve as a reservoir for the infection; a massive tissue would ensue and wall off and isolate the electrode structure into a high impedance dry sack-like formation.

It is also known from the prior art to employ implantable electrodes for stimulating a selected portion of the spinal cord of an animal. Such implantable electrodes included a plurality of flat plate-like electrode portions with upturned lips. Electrodes of this type are disclosed in U.S. Pat. No. 3,724,467 issued Apr. 3, 1973. Also plate-shaped electrodes are mentioned in U.S. Pat. No. 3,089,483 issued May 14, 1963.

SUMMARY OF THE PRESENT INVENTION

The principal object of the present invention is the provision of an improved subcutaneous electrode structure particularly useful for chronic implant and for taking electrocardiograms from active animals.

In one feature of the present invention, the subcutaneous electrode structure includes a thin electrically conductive smooth and inflexible disc having a slot extending inwardly from the periphery thereof with the electrical lead wire extending along the slot end over the terminal and thereof in overlaying relation with the electrically conductive disc to which it is electrically connected, whereby movement of the electrically conductive lead wire is not likely to produce movement of the electrode relative to the tissue.

In another feature of the present invention, the lead wire is electrically insulated from and bonded to the disc by means of an elastomeric material filling the slot and being bonded to the disc for reducing stress on the lead wire and its connection to the disc and for cushioning against pressure points to tissue while permitting a flexible connection to the disc.

In another feature of the present invention, a plurality of apertures are provided around the marginal edges of the slot to permit the electrically insulative potting material to bond to itself through the disc to facilitate bonding of the elastomeric material to the disc.

Other features and advantages of the present invention will become apparent upon a perusal of the following specification taken in conjunction with the accompanying drawings wherein:

BRIEF DESCRIPTION OF THE DRAWINGS

FIG. 1 is a plan view of a prior art small subcutaneous electrode structure employed for taking electrocardiograms of active animals, FIG. 2 is a plan view of a subcutaneous electrode structure incorporating features of the present invention, and FIG. 3 is a sectional view of a portion of the structure of FIG. 2 taken along line 3—3 in the direction of the arrows.

DESCRIPTION OF THE PREFERRED EMBODIMENTS

Referring now to FIG. 1, there is shown the prior art subcutaneous electrode structure 11 employed for taking electrocardiograms from active animals. The prior art electrode structure 11 included a tissue compatible, electrically conductive lead wire 12, as of stainless steel, which was formed into a loop 13 at the sensing end. An electrically insulative jacket 14, as of silicone rubber, was threaded over the wire 12 to the loop 13 for electrically insulating the wire from the tissue except in the loop portion 13. The loop 13 was then sutured to the tissue via sutures 15 and the insulated wire was sutured to the tissue at 16. A typical example of the diameter of the wire loop 13 was 5 mm.

The problem with using the prior art subcutaneous electrodes 11, of the type shown in FIG. 1, is that undesired signal artifacts or noise occurred when recording the electrocardiograms from implanted electrodes 11 in active animals. Important sections of data were obscured or lost completely via the movement artifacts or noise. The origin of these movement artifacts are complex but are associated, in part, with the mechanical and electrical instabilities of the electrodes 11. This problem is common in animal research where the most conventional implantable electrodes are small wires, needles, or wire loops of the type shown in FIG. 1. Firm placement and subsequent tissue imbedding help to reduce movement artifacts, however, it is desired to provide an improved electrode structure which is less susceptible to the production of movement artifacts when taking electrocardiograms and is suited for use in long term studies.

Referring now to FIGS. 2 and 3, there is a subcutaneous electrode structure 17 incorporating features of the present invention. The electrode structure includes a thin, smooth, and rigid disc 18 of an electrically conductive tissue compatible material which is implanted in the animal tissue. Typical examples of tissue compatible, electrically conductive materials include #304 and #316 stainless steel, the latter being preferred in more corrosive environments and when the electrodes are to be in place for substantial periods of time. The use of dissimilar metals should be avoided since unwanted potentials may be caused. Further, electrical performance is improved between electrode pairs if both are constructed from the same piece of material.

The disc 18 is relatively thin having a thickness as of 0.020" and can have diameters from 5 mm to 30 mm (that is, disc areas from 20 to 707 square mm.) depending upon the size of the animal in which the electrode is to be implanted. 5 mm diameter electrodes 17 have been employed for taking electrocardiograms of active rats, whereas up to 30 mm diameter electrodes 17 have been employed for taking electrocardiograms of cattle.

A slot 19 extends radially inward from the periphery of the disc for a distance of approximately ⅓ of the diameter of the disc 18. An electrically conductive wire lead 21, as of tissue compatible stainless steel, is threaded through a length of electrically insulative tubing 22, such as silicone rubber. The insulation 22 is stripped from the terminal end of the wire 21 and the bare wire 21 is threaded over the terminal end of the slot and laced through an aperture 23 centrally located of the disc and thence along the back side of the disc and up through a second aperture 24 spaced from and in alignment with the slot and the first aperture 23. The terminal end of the bare wire is then folded back toward the slot and overlaying the disc 18 and its terminal end is captured in electrically conductive relation to the disc 18 via a tab 25 spot welded to the disc and serving to crimp the terminal end of the wire 21 firmly against the disc 18.

Other crimping tabs or straps 26 and 27, as of the same material as the disc 18 and of the same thickness, preferably obtained by cutting them from the same stock sheet material, extend laterally of the slot 19 and wire 21 for crimping the insulated lead wire 21 in position within the slot 19 so as to be substantially coplanar with the plane of the disc 18. These crimping tabs 26 and 27 are spot welded to the disc 18. Solder and solder flux should be avoided in chronic implants as they are subject to deterioration. The tabs 26 and 27 are provided in pairs with a tab disposed on each side of the disc in registration one with the other, for crimping the insulated wire therebetween.

A plurality of apertures 28 are provided around the marginal edge of the slot 19 and an electrically insulative elastomeric potting material 29, such as room temperature vulcanizing silicone rubber is potted in place over the slot 19, insulated lead wire 21-22, and the regions where the lead wire 21-22 is threaded through the apertures 23 and 24 in the disc and clamped via strap 25 to the disc. In addition, the potting material 29 is faired at 31 into the silicone rubber insulative jacket 22 on the lead wire 21 in the region where the lead wire 21 is joined to the electrode 18. The configuration helps reduce flexure and stress at the junction of the lead wire 21 and the electrode 18 and the fairing of the potting material over the tabs 26, 27 and 25, as well as the terminal end of the wire 21, serve to prevent setting up undesired pressure points when the disc 18 is implanted in tissue.

The strain relief and support at the electrode-lead junction reduces the possibility of artifacts being generated at the contact junctions. A plurality of suture holes 33 are provided around the periphery of the disc 18 to facilitate suturing of the disc 18 to the tissue. The position of the sutures enables the electrode to be implanted firmly and securely.

The electrode does not have irregularities or pores so that it is easy to clean and to keep clean during surgery. Further, it has a low susceptibility to cause localized formation of infection pockets and massive tissue reactions if contamination occurs upon implant. Tissue imbedding is minimal and thus the electrical performance is less likely to change with time. Typically, when an electrode is removed from the implant site, only a thin membranous fascia will be observed around the electrode. Electrodes made in accordance with the invention have proved to be reliable in chronic implants lasting as long as a year.

The advantage to the use of the subcutaneous electrode structure of the present invention, as contrasted with the prior art electrode structure of FIG. 1, for taking electrocardiograms of active animals is that movement artifacts are substantially reduced employing the smooth, rigid disc 18 of the present invention. The reduction of movement artifacts seems best explained in that the smooth, inflexible large area plates 18, rather than the small flexible loops 13, disperse locally created changes in charge concentrations, and minimize net potential changes of the electrode by allowing large sampling across locally created positive and negative differentials. The smooth surface minimized effective surface area per unit of distributed surface area exposed to mechanical stress. The smoothness is also believed to promote uniformity in charge distribution at the interface and decrease turbulence during movements. The inflexibility of the disc reduces surface stress, and a reduction of mechanical stress of any initially present differential charge distribution should in effect limit the rate and the quantity of unidirectional reaction that is induced by stress. Further, the large area of the electrode may reduce pressure per unit area on surrounding tissue and thus prevent transmembrane potential variations of the tissue, a biological source of movement artifacts. The electrode provides a way of reducing movement artifacts other than by trying to avoid the disturbance.

In an in vivo test a pair of wire loop type electrodes, like in FIG. 1, was placed subcutaneously. The electrode leads were then pulled so as to cause the electrodes to drag across the tissue. A pair of subject electrodes was treated similarly and it was discovered that the artifacts produced by the moving subject electrodes were very minor compared to those generated by the wire loop electrodes as they moved across the tissue.

In a second test, an in vitro test, a pair of the wire loop electrodes (FIG. 1) was placed in 0.9% saline and one electrode was rubbed with a finger. The electrical output from the electrodes was monitored as the rubbing took place. Next, a pair of subject electrodes was similarly treated. The electrodes made in accordance with the subject invention produced a base potential difference that gradually rose to a plateau of about 50 mv and then decayed slowly toward zero when the rubbing disturbance was stopped. During the disturbance, there were superimposed on the base potential relatively smooth and small oscillations of about 100 microvolts. A similar gradual change in base potential difference was noted with the lead extension electrodes; however, superimposed on the base change were spikes approximately six millivolts in amplitude.

What is claimed is:

1. In a subcutaneous electrode structure:
   electrode means including an electrically conductive plate-shaped structure for implanting in electrically conductive relation with subcutaneous tissue of an animal to which an electric connection is to be established;
   electrical conductor means including an electrically conductive wire structure for making electrical connection to said electrode means;
   said plate-shaped structure including an elongated slot extending into said plate-shaped structure from the periphery thereof, said slot having a peripheral end and an inner end;
   said electrical conductor means extending along said slot and over the inner end of said slot and being disposed overlaying said plate-shaped structure, said wire structure being electrically conductively connected to said underlying portion of said plate-shaped structure; and
   electrical insulative means for enveloping that portion of said electrically conductive wire structure extending along said slot and overlaying at least a portion of said plate-shaped structure for electrically insulating portions of said wire structure from the subcutaneous tissue.

2. The apparatus of claim 1 wherein said electrically insulative means comprises a flexible elastomeric material bonded to said plate-shaped structure and covering portions of said wire structure.

3. The apparatus of claim 2 wherein said flexible elastomeric material is silicone rubber.

4. The apparatus of claim 2 including a plurality of holes provided in said plate-shaped structure along the marginal lip of said slot receiving said elastomeric material therewithin to facilitate bonding thereof to said plate-shaped structure.

5. The apparatus of claim 1 including a plurality of spaced holes in said plate-shaped structure, said holes being disposed in general alignment with the longitudinal axis of said slot and said holes having said electrical wire structure woven therethrough to facilitate making of the electrical connection between said wire structure and said plate-shaped structure.

6. The apparatus of claim 5 including a plurality of holes disposed about the periphery of said plate-shaped structure to facilitate suturing of said electrode means to the tissue.

7. The apparatus of claim 5 wherein said slot is directed generally radially of said electrode means.

8. The apparatus of claim 1 wherein said electrode means is made of stainless steel.

9. The apparatus of claim 1 wherein said plate-shaped structure has a major face with an area of between 20 and 707 square mm.

10. The apparatus of claim 1 wherein said electrical conductor means extends away from said plate-shaped structure in a direction generally aligned with the longitudinal axis of said slot and in a plane substantially coplanar with said plate-shaped structure.

11. The apparatus of claim 1 including a plurality of tab means extending over and laterally of said slot and wire structure for capturing said wire structure within said slot and in a position substantially coplanar with said plate-shaped structure.

* * * * *